(12) United States Patent
Velasco Alvarez et al.

(10) Patent No.: US 8,647,849 B2
(45) Date of Patent: Feb. 11, 2014

(54) BIODIESEL PRODUCTION METHOD

(75) Inventors: Javier Velasco Alvarez, Armilla-Granada (ES); José Luis Adrio Fondevila, Armilla-Granada (ES); M'del Carmen Ronchel Barreno, Armilla-Granada (ES); Alberto Zafra Gómez, Armilla-Granada (ES); Magdalena Valdivieso Ugarte, Armilla-Granada (ES)

(73) Assignee: Neol Biosolutions, S.A., Armilla (Granada) (ES)

( * ) Notice: Subject to any disclaimer, the term of this patent is extended or adjusted under 35 U.S.C. 154(b) by 459 days.

(21) Appl. No.: 12/934,092

(22) PCT Filed: Mar. 25, 2009

(86) PCT No.: PCT/ES2009/000167
§ 371 (c)(1),
(2), (4) Date: Dec. 15, 2010

(87) PCT Pub. No.: WO2009/118438
PCT Pub. Date: Oct. 1, 2009

(65) Prior Publication Data
US 2011/0088312 A1     Apr. 21, 2011

(30) Foreign Application Priority Data
Mar. 25, 2008  (ES) .................................. 200800923

(51) Int. Cl.
*C12P 7/64*     (2006.01)
*C12P 1/00*     (2006.01)

(52) U.S. Cl.
USPC ........................................... 435/134; 435/41

(58) Field of Classification Search
USPC ................................................ 435/41, 134
See application file for complete search history.

(56) References Cited

U.S. PATENT DOCUMENTS

2001/0049133 A1   12/2001   McCabe et al.

FOREIGN PATENT DOCUMENTS

| WO | 0154510 A1 | 8/2001 | |
| WO | 02064802 A2 | 8/2002 | |
| WO | 02077293 A2 | 10/2002 | |
| WO | 2006136311 A1 | 12/2006 | |
| WO | 2008011811 A1 | 1/2008 | |
| WO | WO 2008/134836 | * 11/2008 | ............... C10L 1/02 |

OTHER PUBLICATIONS

Pan et al. "Isolation of the Oleaginous Yeasts from the Soil and Studies of Their Lipid-Producing Capacities" Food Technol. Biotechnol. 47 (2) 215-220 Apr.-Jun. 2009.*
Németh, A. et al., "Development of a New Bioprocess for Production of 1,3-propanediol I.: Modeling of Glycerol Bioconversion to 1,3-propanediol with *Klebsiella pneumoniae* Enzymes", 2008, Applied Biochemistry and Biotechnology, vol. 144, No. 1, pp. 47-58.
Yonghong Li et al., "High-density cultivation of oleaginous yeast *Rhodosporidium toruloides* Y4 in fed-batch culture", 2007, Enzyme and Microbial Technology, vol. 41, 3, pp. 312-317.
Turcotte, G. et al., "Biosynthesis of lipids by *Rhodosporidium toruloides* ATCC 10788", 1998, Journal of Biotechnology, vol. 8. 3, pp. 221-237.
Shah, S. et al., "Biodiesel Preparation by Lipase-Catalyzed Transesterification of Jatropha Oil", Energy and Fuels, 2004, 18, 154-159.
Karmee, S.K. et al., "Preparation of biodiesel from crude oil of *Pongamia pinnata*", 2005, Bioresource Technology, 96, 1425-1429.
Ghadge, S.V. et al., "Process optimization for biodiesel production from mahua (*Madhuca indica*) oil using response surface methodology", Bioresource Technology, 2006, 97, 379-384.
Ratledge, C., "Microorganisms for lipids", Acta Biotechnologica, 1991, 11, 429-438.
Ratledge, C., "Fatty acid biosynthesis in microorganisms being used for Single Cell Oil production", Biochimie, 2004, 86, 807-815.
Miao, X. et al., "Biodiesel production from heterotrophic microalgal oil", Bioresource Technology, 2006, 97, 841-846.
Liu, B. et al., "Biodiesel production by direct methanolysis of oleaginous microbial biomass", Journal of Chemical Technology and Biotechnology, 2007, 82, 775-780.

* cited by examiner

*Primary Examiner* — Thane Underdahl
(74) *Attorney, Agent, or Firm* — Tristan A. Fuierer; Moore & Van Allen, PLLC

(57) ABSTRACT

The present invention relates to a process for obtaining a mixture of fatty acid esters, suitable as a combustible or fuel in diesel cycle engines, comprising: a) the obtaining of a microbial biomass with a triglyceride content equal to or greater than 20% by dry weight, by means of the use of an oleaginous microorganism using glycerin as a carbon source; and b) the conversion of the triglycerides contained in the biomass obtained in step a) into a mixture of fatty acid esters. The invention likewise relates to said oleaginous microorganism, to a process for its selection and to polynucleotides obtained therefrom.

7 Claims, No Drawings

SEQUENCE LISTING

<160> NUMBER OF SEQ ID NOS: 8

<210> SEQ ID NO 1
<211> LENGTH: 550
<212> TYPE: DNA
<213> ORGANISM: Rhodosporidium toruloides

<400> SEQUENCE: 1

```
gcatcctaag cgtgaaggac cgaagccctc gccatacggc acgctgcgtt cctcagtccc      60
ccaggacgta tccagcagaa agctataaca cagccgagac tgctacattc taactgccat     120
tatccgcccc ggaaaactga tgctggcctg caaaccgagc aagcccggca agcaagtctg     180
acttcaagcg tttcccttcc aacaatttca cgtacttttta actctctttc caaagtgctt     240
ttcatctttc cctcacggta cttgttcgct atcggtctct cgccaatatt tagctttaga     300
tggaatttac cacccaattt gagctgcatt cccaaacaac tcgactcgtc gaaagtgtat     360
cacaaagcgc tgggcgtccg caccgtgtaa tggggtatca ccactatgcc gctgtattcc     420
aacagacttg tgtgcggtcc aacgcggaaa acacttctag agattacaac tcggacaccg     480
aaggtgccag attacaaatt tgagctcttc ccgcttcgct cgccgctact aggggaatcc     540
ttgttagttt                                                            550
```

<210> SEQ ID NO 2
<211> LENGTH: 560
<212> TYPE: DNA
<213> ORGANISM: Rhodosporidium toruloides

<400> SEQUENCE: 2

```
aggtgtccac ttaacttgga gcccgaccct cactttctaa ccctgtgcat tgtcttggg      60
tagtagcttg cgtcagcgag cgaatcccat ttacttaca aacacaaagt ctatgaatgt     120
aacaaattta taacaaaaca aaactttcaa caacggatct cttggctctc gcatcgatga     180
agaacgcagc gaaatgcgat acgtaatgtg aattgcagaa ttcagtgaat catcgaatct     240
ttgaacgcac cttgcgctcc atggtattcc gtggagcatg cctgtttgag tgtcatgaat     300
tcttcaaccc acctctttct tagtgaatca ggcggtgttt ggattctgag cgctgctggc     360
ttcgcggcct agctcgctcg taatgcatta gcatccgcaa tcaaacttcg gattgactcg     420
gcgtaataga ctattcgctg aggattctgg tctctgactg gagccgggta aggttaaagg     480
gagctactaa tcctcatgtc tatcttgaga ttagacctca aatcaggtag gactacccgc     540
tgaacttaag catatcaata                                                 560
```

<210> SEQ ID NO 3
<211> LENGTH: 550
<212> TYPE: DNA
<213> ORGANISM: Rhodosporidium toruloides

<400> SEQUENCE: 3

```
gcatcctaag cgtgaagggc cgaagccctc gccatacggc acgctgcgtt cctcagtccc      60
ccaggacgta tccagcagaa agctataaca cagccgagac tgctaccttc taactgccat     120
tatccgcccc ggaaaactga tgctggcctg caaaccgagc aagcccggca agcaagtctg     180
acttcaagcg tttcccttcc aacaatttca cgtacttttta actctctttc caaagtgctt     240
ttcatctttc cctcacggta cttgttcgct atcggtctct cgccaatatt tagctttaga     300
tggaatttac cacccaattt gagctgcatt cccaaacaac tcgactcgtc gaaagtgtat     360
```

```
cacaaagcgc tgggcgtccg caccgtgtaa tggggtatca ccactatgcc gctgtattcc     420
aacagacttg tgtgcggtcc aacgcggaaa acacttctag agattacaac tcggacaccg     480
aaggtgccag attacaaatt tgagctcttc ccgcttcgct cgccgctact aggggaatcc     540
ttgttagttt                                                            550

<210> SEQ ID NO 4
<211> LENGTH: 561
<212> TYPE: DNA
<213> ORGANISM: Rhodosporidium toruloides

<400> SEQUENCE: 4
ggcgtccact taacttggag cccgaccctc actctctaac cctgtgcact tgtcttgggt      60
agtagcttgc gcaagcgagc gaatcccatt tcacttacaa acacgaagtc aatgaatgta     120
acaaatttat aacaaaacaa aactttcaac aacggatctc ttggctctcg catcgatgaa     180
gaacgcagcg aaatgcgata cgtaatgtga attgcagaat tcagtgaatc atcgaatctt     240
tgaacgcacc ttgcgctcca tggtattccg tggagcatgc ctgtttgagt gtcatgaatt     300
cttcaaccca cctctttctt agtgaatcag gcggtgtttg gattctgagc gctgctggcc     360
tcacagccta gctcgctcgc aatgcattag catccgcaat cgaacttcgg attgactcgg     420
cgtaatagac tattcgctga ggattctggt ctctgactgg agccgggtga gatcaaagga     480
agctactaat cctcatgtct atcttgagat tagacctcaa atcaggtagg actacccgct     540
gaacttaagc atatcaataa g                                              561

<210> SEQ ID NO 5
<211> LENGTH: 24
<212> TYPE: DNA
<213> ORGANISM: Artificial Sequence
<220> FEATURE:
<223> OTHER INFORMATION: Synthetic Construct

<400> SEQUENCE: 5
gcatatcaat aagcggagga aaag                                            24

<210> SEQ ID NO 6
<211> LENGTH: 19
<212> TYPE: DNA
<213> ORGANISM: Artificial Sequence
<220> FEATURE:
<223> OTHER INFORMATION: Synthetic Construct

<400> SEQUENCE: 6
tccgtaggtg aacctgcgg                                                  19

<210> SEQ ID NO 7
<211> LENGTH: 19
<212> TYPE: DNA
<213> ORGANISM: Artificial Sequence
<220> FEATURE:
<223> OTHER INFORMATION: Synthetic Construct

<400> SEQUENCE: 7
ggtccgtgtt tcaagacgg                                                  19

<210> SEQ ID NO 8
<211> LENGTH: 20
<212> TYPE: DNA
```

```
<213> ORGANISM: Artificial Sequence
<220> FEATURE:
<223> OTHER INFORMATION: Synthetic Construct

<400> SEQUENCE: 8
tcctccgctt attgatatgc                                          20
```

BIODIESEL PRODUCTION METHOD

CROSS-REFERENCE TO RELATED APPLICATIONS

This application is filed under the provisions of 35 U.S.C. §371 and claims the priority of International Patent Application No. PCT/ES2009/000167 filed on 25 Mar. 2009 entitled "Improved Biodiesel Production Method" in the name of Javier Velasco Alvarez, et al., which claims priority of Spanish Patent Application No. P200800923 filed on 25 Mar. 2008, both of which are hereby incorporated by reference herein in their entirety.

FIELD OF THE ART

The present invention relates to a process for obtaining fuel for diesel cycle engines from oils of a microbial origin, as well as to the microorganisms producing said oils. The invention is likewise aimed at said oleaginous microorganism, to a process for its selection and to polynucleotides obtained therefrom.

STATE OF THE ART

The current production of biodiesel is based on the transesterification (or alcoholysis) of triglycerides of a plant origin (sunflower, rapeseed, palm and other species) with low molecular weight alcohols (methanol, ethanol) to produce fatty acid methyl/ethyl esters and glycerin. The esterification reaction is feasible with any alcohol but virtually only methanol and ethanol are used for this process (EP 523 767). Methyl alcohol is the most used due to its low cost and to its physical-chemical properties allowing reacting with any low acid oil.

The production of biodiesel is performed from triglycerides and alcohol, combining them in a 10/1 ratio by weight. Therefore, starting from 1 ton of oil, approximately 1 ton of biodiesel and about 100 kg of crude glycerin are obtained.

Crude glycerin, with a purity of 70-85%, can be purified by means of a conditioning phase wherein, in addition to a step of neutralization, an evaporation is performed for the purpose of increasing its concentration until reaching 90-95%. Finally, this concentrated product is purified through columns, high purity glycerin being obtained the destination of which is mainly the pharmaceutical and cosmetic industry. However, the recent growth of the biodiesel market, over 50% per year, has generated the saturation of the world market for glycerin. This situation will become worse in a near future if the objectives of replacing current fuels with biofuels established by Public Organisms are complied with, giving rise to a surplus of crude glycerin in world markets. In this situation its commercial recovery by means of purification, does not seem the most attractive solution for biodiesel plants, since the process of purification is too expensive to compete in a saturated market. Due to this situation, other applications such as its possible use as a fuel have started to be considered, despite the drawbacks from the environmental point of view.

In addition, the current biodiesel production process, mostly from oleaginous seeds or vegetable oils, depends to a great extent on the price of these raw materials which involve between 50-60% of the production costs. Although the use of used oils, or another type of fat, may reduce the price of the raw material, this process requires a series of additional steps to refine these oils. It is therefore necessary to explore new strategies for reducing the price of biodiesel, especially those that decrease the number of steps, improve the yields, and use less expensive raw materials.

The use of inedible oils has recently been proposed as alternative reserves for producing biodiesel, particularly oils from *Jatropa curcas, Pongamia pinnata* or *Madhuca indica* seeds (Shah et al., Energy fuels, 2004, 18, 154-159; Karmee S K et al., 2005, Bioresource Technol, 96, 1425-1429; Ghadge S V et al., Bioresource Technol, 2006, 97, 379-384). However, these alternatives are not viable in all the countries due to climatic or geographic conditions.

The current production of triglycerides from oleaginous arable crops or from ligneous plants with high oil content is of about 120 million tons per year. If the expectations of growth of the biodiesel market are fulfilled, the supply of these triglycerides will be in an extreme situation, even being able to jeopardize the supply of food and the traditional oleochemical industry. The production of more crops of this type requires a large amount of arable land, a situation which is not possible in many regions.

Therefore, the biodiesel industry needs alternative reserves of triglycerides which can be obtained by other routes and, especially, those which can operate continuously and without requiring large arable areas.

The production of lipids from microorganisms has been an object of research for a long time. Some fungi, yeasts and algae have the capacity to intracellularly accumulate up to more than 70% of their biomass in the form of lipids (Ratledge C, Acta Biotechnol, 1991, 11, 429-438) during periods of metabolic stress, therefore, in a similar way to what occurs with plant seeds, they are called oleaginous microorganisms (Ratledge, Biochemie, 2004, 86, 807-815).

Some yeasts belonging to the *Rhodotorula, Rhodosporidium, Yarrowia, Cryptococcus, Debaryomyces, Candida* or *Lypomyces* genera and some microalgae of the *Chlorella* genus accumulate triglycerides containing profiles of fatty acids of the C16 and C18 series (for example, palmitic, stearic, oleic) very similar to those present in vegetable oils as, for example, rapeseed or soybean. Therefore, oils from these microorganisms (oils of a microbial origin, SCO) could potentially be used to produce biodiesel, as they would comply with the standards indicated in the standard EN 14214.

There is little information about the production of biodiesel from lipids produced by microorganisms. A process using the microalga *Chorella starkey* (Bioresource Technol, 2006, 97, 841-846) and another process with yeasts (J Chem Technol Biotechnol, 2007, 82, 775-780) have recently been described. However, in both cases the raw material used was glucose therefore the economic balance of the process is not viable.

Organic byproducts/waste generated from industrial processes of the agrifood, forest or industrial sectors can be used as raw material for producing higher value-added compounds by means of using microorganism or enzymes. Crude glycerin from the biodiesel industry would be included among these byproducts.

Based on these background documents, it would be necessary to develop improved processes in the biodiesel industry which solve, from the strategic, economic and technical point of view:

The problems generated by the huge surpluses of crude glycerin.

The drawback of using raw materials involving a high price or large arable areas.

BRIEF DESCRIPTION OF THE INVENTION

The authors of the present invention have developed a novel process for the production of a biodiesel fuel from glycerin as a carbon source, achieving a process with yields similar to the established processes, but improving the quality of the product and the cost of the production process. The process specifically allows obtaining a mixture of fatty acid esters, suitable as a combustible or fuel for diesel type engines, from microbial biomass with a high triglyceride content.

Thus, a first aspect of the present invention is aimed at a process for obtaining biodiesel comprising:
  a) the obtaining of a microbial biomass with a triglyceride content equal to or greater than 20% by dry weight, by means of the use of an oleaginous microorganism using glycerin as a carbon source;
  b) the conversion of the triglycerides contained in the biomass obtained in step a) into a mixture of fatty acid esters.

In a particular embodiment, the microbial biomass obtained in section a) is subjected to a separation of triglycerides contained therein, which are subsequently converted into a mixture of fatty acid esters according to step b).

In a particular embodiment, in step a) a microbial biomass with a triglyceride content between 20% and 70% by dry weight is obtained.

In another particular embodiment of the invention, oleaginous plant seeds are added to the microbial biomass, prior to the obtaining of the mixture of fatty acid esters.

The invention is likewise aimed at a process for obtaining biodiesel comprising:
  a. the obtaining of a microbial biomass with a triglyceride content equal to or greater than 20% by dry weight, by means of the use of an oleaginous microorganism using glycerin as a carbon source;
  b. optionally, the separation of the triglycerides from the microbial biomass;
  c. the conversion of the triglycerides contained in the biomass obtained in step a) or of the triglycerides separated in step b) into a mixture of fatty acid esters by means of alcoholysis in acid medium, such that a phase comprising fatty acid esters and another phase comprising glycerin and cell remains are obtained;
  d. a first separation of the phase comprising fatty acid esters and the phase comprising glycerin and cell remains obtained in step c);
  e. the neutralization of the phase comprising the fatty acid esters separated in step d), such that a phase comprising fatty acid esters and a phase comprising water and alcohol remains are obtained;
  f. a second separation of the phase comprising fatty acid esters and the phase comprising water and alcohol remains obtained in step e);
  g. purification of the phase comprising fatty acid esters separated in step f).

In an additional aspect, the invention is aimed at an oleaginous microorganism capable of accumulating triglycerides using glycerin as a carbon source.

Another additional aspect of the invention relates to a process for selecting oleaginous microorganisms capable of accumulating triglycerides using glycerin as the only carbon source comprising:
  (i) obtaining strains capable of growing in glycerin as the only carbon source;
  (ii) selecting the triglyceride-producing strains of step (i).

DETAILED DESCRIPTION OF THE INVENTION

In the present invention, the terms "biomass" or "microbial biomass" refer to the set of cells of the microorganism once grown in the culture medium.

The biodiesel is a biofuel, renewable fuel, described according to the ASTM (American Society for Testing and Materials) specifications as monoalkyl esters of long chain fatty acids (with 8 or more carbons) derived from renewable lipids such as vegetable oils or animal fats, and which are used in compression ignition engines (diesel engines). In the present invention, the oils come from the previously defined microbial biomass.

In the present invention, "oleaginous microorganism" relates to a yeast, filamentous fungus or microalga having the capacity to intracellularly accumulate lipids during periods of metabolic stress (*Rhodotorula*, *Rhodosporidium*, *Yarrowia*, *Cryptococcus*, *Debaryomyces*, *Candida*, *Lypomyces* or *Chlorella*).

In a first aspect, the present invention is aimed at a process for obtaining biodiesel comprising:
  a) the obtaining of a microbial biomass with a triglyceride content equal to or greater than 20% by dry weight, by means of the use of an oleaginous microorganism using glycerin as a carbon source;
  b) the conversion of the triglycerides contained in the biomass obtained in step a) into a mixture of fatty acid esters.

In a particular embodiment, the microbial biomass obtained in section a) is subjected to a separation of the triglycerides contained therein, which are subsequently converted into a mixture of fatty acid esters. This separation preferably comprises an extraction.

The process for obtaining the microbial biomass in step a) involves the culture of oleaginous microorganisms in flasks or bioreactors until reaching a triglyceride content equal to or greater than 20% by dry weight.

In a particular embodiment, the microorganisms are cultured for 2-5 days at a temperature between 18° C. and 30° C., preferably between 23° C. and 30° C. with constant stirring. Once the maximum intracellular amount of triglycerides is reached, the cells are collected by means of any of the processes normally used for this purpose such as, for example, filtration or centrifugation.

In a particular embodiment, the triglyceride content reached in the biomass is comprised between 20% and 70% of the dry weight.

In a preferred embodiment of the invention, the microorganism used to produce biomass is a yeast. In even more preferred embodiments, the yeast is of the *Rhodosporidium* genus and the *Rhodosporidium toruloides* CECT 13006 and *Rhodosporidium toruloides* CECT 13007 strains are especially preferred.

The microorganisms are grown in culture media in which glycerin is present as a carbon source, which glycerin is in excess in relation to the nitrogen source present in the same medium, the latter being able to be yeast extract, peptone, corn steep liquor, urea, sodium glutamate or inorganic nitrogen sources such as different ammonium salts, although it is not limited thereto.

In addition to glycerin, other carbon sources, such as for example although without limitation, glucose, molasses, sucrose, fructose, starches or fatty acids, can be present in the culture medium. According to a particular embodiment of the invention, glycerin is used as a carbon source in the fermentation medium, preferably in an amount involving between 70-100% of the total of the carbohydrates used. For economic reasons, it is preferred that the glycerin used is crude glycerin, i.e., having a purity between approximately 70% and 85%.

In another particular embodiment of the invention, the process of the invention additionally comprises the addition of oleaginous plant seeds to the microbial biomass obtained in step a) as a step prior to the obtaining of the mixture of fatty acid esters. Suitable plant seeds are sunflower, rapeseed, palm, soybean, turnip rape or coconut seeds, for example.

The mixture of the fatty acid esters is in turn prepared by means of alcoholysis of the triglycerides contained in the microbial biomass obtained in step a) directly or on the triglycerides once they are separated from the microbial biomass. A catalyst can be used in this reaction to improve the rate and the final yield. The alcoholysis is preferably performed in acid medium, i.e., it uses an acid as the catalyst. The acidification can be performed by means of the use of any acid such as, for example, sulfuric acid, hydrochloric acid or phosphoric acid, although it is not necessarily limited thereto. The alcohol used in the reaction is preferably in an excess of between 5 and 40 times by weight with respect to the biomass, more preferably between 10 and 30 times. In a particular embodiment, the reaction is allowed to proceed with constant stirring for between 20 and 36 hours, at a temperature between 40° C. and 70° C., preferably between 50° C. and 70° C. Also preferably, the alcoholysis of the biomass is performed with alcohols having 1, 2, 3 or 4 carbons. Even more preferably, the alcohol is methanol or ethanol, methanol being the more preferred alcohol.

In addition to the previously indicated homogeneous acid type catalysts, in other embodiments of the invention heterogeneous acid catalysts (for example, Zeolites, Sulfonic Resins, $SO_4/ZrO_2$, $WO_3/ZrO_2$), heterogeneous basic catalysts (for example, MgO, CaO, Na/NaOH/Al$_2$O$_3$), homogeneous basic catalysts (for example, KOH, NaOH) or enzyme catalysts (Lipases, such as for example: *Candida*, *Penicillium*, *Pseudomonas*) are used.

The invention is likewise aimed at a process for obtaining biodiesel comprising:
  a. the obtaining of a microbial biomass with a triglyceride content equal to or greater than 20% by dry weight, by means of the use of an oleaginous microorganism using glycerin as a carbon source;
  b. optionally, the separation of the triglycerides from the microbial biomass;
  c. the conversion of the triglycerides contained in the biomass obtained in step a) or of the triglycerides separated in step b) into a mixture of fatty acid esters by means of alcoholysis in acid medium, such that a phase comprising fatty acid esters and another phase comprising glycerin and cell remains are obtained;
  d. a first separation of the phase comprising fatty acid esters and the phase comprising glycerin and cell remains obtained in step c);
  e. the neutralization of the phase comprising the fatty acid esters separated in step d), such that a phase comprising fatty acid esters and a phase comprising water and alcohol remains are obtained;
  f. a second separation of the phase comprising fatty acid esters and the phase comprising water and alcohol remains obtained in step e);
  g. the purification of the phase comprising fatty acid esters separated in step f).

Steps a), b) and c) are carried out as has been previously described.

In a particular embodiment of the invention, step d) of separation of the phases is performed by means of a centrifugation process.

Step e) of neutralization of the phase comprising the fatty acid esters serves to remove the excess of alcohol and, where appropriate, of acid. The neutralization is suitably performed by adding a solution of a weak base such as, for example, sodium hydroxide, potassium hydroxide or ammonium hydroxide, to a certain amount of water which preferably ranges between ⅓ and 1/10 by volume of the amount of phase comprising the fatty acid esters separated in step d). In a particular embodiment of the invention, said neutralization can be carried out in several steps, for example a first step wherein a base concentration of 0.05-0.3% by weight over the water added is used and a second step using between 0.01 and 0.1% by weight over the water added.

In a particular embodiment, during this neutralization step a mechanical stirring is carried out for a time of about 15-60 minutes at a regulated speed to prevent the formation of emulsions.

In a particular embodiment, the second separation of the phases carried out in step f) is performed by means of gravity decantation, a phase formed by water and alcohol remains and a phase containing the fatty acid esters being obtained.

Said esters can be purified by means of the elimination of water and alcohol remains in an evaporator. The evaporation of small amounts of water and the alcohol, frequently methanol or ethanol, provides a process with lower energy demand since it requires temperatures lower than those used for the distillation of the esters during the purification thereof.

The biodiesel thus obtained can be recirculated if it has a water content greater than the established by the Standard 14214.

Oleaginous Microorganisms

As has been previously indicated, the process for obtaining biodiesel comprises the use of an oleaginous microorganism using glycerin as a carbon source. Therefore, in an additional aspect, the invention is aimed at an oleaginous microorganism capable of accumulating triglycerides using glycerin as a carbon source.

In another particular embodiment, the microorganism is capable of accumulating a triglyceride content equal to or greater than 20% by dry weight, preferably between 20% and 70%.

In the context of the present invention, the oleaginous microorganism can be a yeast, a filamentous fungus or a microalga. In a preferred embodiment of the invention, the microorganism is a yeast. In even more preferred embodiments, the yeast is of the *Rhodosporidium* genus and the *Rhodosporidium toruloides* CECT 13006 and *Rhodosporidium toruloides* CECT 13007 strains are especially preferred.

The international depositary authority for the microorganisms of the invention has been the Spanish Type Culture Collection (Colección Española de Cultivos Tipo—CECT).

In another additional aspect, the invention provides a process for the selection of oleaginous microorganisms capable of accumulating triglycerides using glycerin as the only carbon source comprising:
  (i) obtaining strains capable of growing in a culture medium comprising glycerin as the only carbon source;
  (ii) selecting the triglyceride-producing strains of step (i).

In step (i), any culture medium of glycerin known in the art can be used for selecting strains, for example *Rhodotorula, Rhodosporidium, Yarrowia, Cryptococcus, Debaryomyces, Candida* or *Lypomyces* or *Chlorella*. The culture medium of glycerin preferably comprises MMG medium (per liter: yeast nitrogen base (YNB) without amino acids, 6.7 g; crude glycerin, 47 g; supplemented with chloramphenicol (50 µg/mL).

In step (ii), the selection of triglyceride-producing strains can be carried out by means of a sampling using a staining, for example, with Nile red and subsequent fluorescence analysis.

The yeast strains defined in the present invention have been identified through the nucleotide sequences corresponding to the D1/D2 region of ribosomal DNA subunit 26S and to a fragment of the total ITS region located between subunits 18S and 26S.

Therefore, in another aspect, the invention relates to a polynucleotide characterized by having the sequence shown in SEQ ID NO: 1, corresponding to the D1/D2 region of ribosomal DNA subunit 26S of *Rhodosporidium toruloides* CECT 13006.

In another aspect, the invention relates to a polynucleotide characterized by having the sequence shown in SEQ ID NO: 2, corresponding to the total ITS region located between subunits 18S and 26S of *Rhodosporidium toruloides* CECT 13006.

In another aspect, the invention relates to a polynucleotide characterized by having the sequence shown in SEQ ID NO: 3, corresponding to the D1/D2 region of ribosomal DNA subunit 26S of *Rhodosporidium toruloides* CECT 13007.

In another aspect, the invention relates to a polynucleotide characterized by having the sequence shown in SEQ ID NO: 4, corresponding to the total ITS region located between subunits 18S and 26S of *Rhodosporidium toruloides* CECT 13007.

As understood by the person skilled in the art, the polynucleotides of the invention can be used as probes, or to design primers or probes therefrom, for identifying other species of the *Rhodosporidium* genus.

EXAMPLES

1. Selection of Microorganisms Capable of Growing in Crude Glycerin as the Only Carbon Source These microorganisms were isolated by means of two strategies from soil samples taken in the Río Tinto (Huelva) riverbanks. 10 mL of saline solution were added to 1 g of sample placed in a test tube and it was vigorously stirred for 10 minutes. From this suspension, 1:10 serial dilutions in saline solution were prepared, 0.1 mL being seeded in plates containing YPG medium (per liter: yeast extract, 10 g; bacteriological peptone, 20 g; crude glycerin, 47 g; supplemented with chloramphenicol (50 μg/mL)) to inhibit the bacterial growth. The plates were incubated at 28° C. for 4-5 days and the grown colonies were transferred to plates with MMG medium (per liter: yeast nitrogen base (YNB) without amino acids, 6.7 g; crude glycerin, 47 g; supplemented with chloramphenicol (50 μg/mL)). The plates were incubated at 28° C. for 5-7 days.

In the second strategy, a portion of a sample was ground in a sterile mortar and 1 g thereof was added to a flask containing 50 mL of MMG medium supplemented with rose bengal (50 μg/mL) and chloramphenicol (50 μg/mL). The flask was incubated at 28° C. and 250 rpm for 24 hours. Then, 0.5 mL of this culture were transferred to another flask containing MMG with 8% crude glycerin, being incubated in the same conditions. This process was repeated again but using MMG medium containing 12% crude glycerin. From the cultures containing 8-12% glycerin, dilutions were seeded in plates with MMG medium. These were incubated at 28° C. for 7 days.

By means of these two processes, 470 colonies in the YPG medium were obtained, from which 230 capable of growing in MMG were selected.

2. Selection of Microorganisms Capable of Growing in Crude Glycerin as the Only Carbon Source and Accumulating Triglycerides The capacity to accumulate triglycerides was analyzed by means of a sampling using the Nile red staining (Kimura K, et al., 2004, *J. Microbiol. Methods*, 56, 331-338).

Cultures were grown in MMG medium on a small scale (1 mL) in 96-well plates at 28° C., 250 rpm for 72 hours. After this time, 0.5 mL of culture were taken which were diluted in the same volume of PBS buffer (10 mM potassium phosphate buffer, 0.15 M KCl, pH 7.0). 0.01 mL of a Nile red solution (0.5 μLg/mL) were added to 0.4 mL of this suspension, the mixture was incubated at room temperature for 5 minutes and 0.1 mL were transferred to a microtiter plate, the fluorescence being measured in a plate reader at 600 nm. Twelve cultures showed a greater fluorescence measurement than the strain used as control, *Rhodosporidium toruloides* CBS14, and were selected as possible triglyceride producers. These twelve strains and the control were cultured, in triplicate, at 28° C., 250 rpm for 96 hours in flasks containing 50 mL of MEM medium (for 1 liter: crude glycerin, 47 g; yeast extract, 1.5 g; monopotassium phosphate, 0.75 g; ammonium nitrate, 0.28 g; $CaCl_2.2H_2O$, 0.4 g; and $MgSO_4.72H_2O$, 0.4 g, adjusted to pH 5 with concentrated HCl). The cells were collected by centrifugation, two tubes were drained and dried in an oven at 50° C. for 24 hours to determine the dry weight. The other tube was drained on filter paper and the cells were resuspended in 5 mL of water containing 0.75 mL of ammonium hydroxide. The suspension was gently stirred and incubated in a bath at 60-70° C. for 15 minutes. It was cooled and 5 mL of ethanol were added, stirring vigorously. Then, 12.5 mL of ethyl ether were added, it was briefly stirred and the same volume of petroleum ether was added. The mixture was separated by centrifugation, the organic phase being removed to a flat-bottomed spherical flask. The organic phase was evaporated to dryness in a rotary evaporator and the flask was introduced in an oven at 102° C. until obtaining a constant weight.

By means of this measurement by gravimetry, two strains capable of accumulating 25.3% and 27.2% of their dry weight in the form of triglyceride matter were identified. Both were identified, by means of sequencing the D1/D2 region of ribosomal DNA subunit 26S and a fragment of the total ITS (Internal Transcribed Spacer) region located between subunits 18S and 26S, as two different *Rhodosporidium toruloides* strains also showing differences in relation to the sequences of this species deposited in the existing databases. Both strains have been deposited on Jan. 16, 2008 in the Spanish Type Culture Collection (CECT), University of Valencia, Spain, as *Rhodosporidium toruloides* 0376 (accession number CECT no. 13006) and *Rhodosporidium toruloides* 0770 (accession number CECT no. 13007), in accordance with the Budapest Treaty.

To amplify the D1/D2 zone corresponding to ribosomal DNA subunit 28S, the oligonucleotides of sequences SEQ ID NO: 5 and SEQ ID NO: 7 have been used. Likewise, the total ITS region located between subunits 18S and 26S was amplified using the oligonucleotides of sequences SEQ ID NO: 6 and SEQ ID NO: 8.

In another aspect, the invention relates to an oligonucleotide characterized by having the sequence shown in SEQ ID NO: 5.

In another aspect, the invention relates to an oligonucleotide characterized by having the sequence shown in SEQ ID NO: 6.

In another aspect, the invention relates to an oligonucleotide characterized by having the sequence shown in SEQ ID NO: 7.

In another aspect, the invention relates to an oligonucleotide characterized by having the sequence shown in SEQ ID NO: 8.

3. Production of Biodiesel by the Fermentation of Microorganisms Capable of Growing in Crude Glycerin as the Only Carbon Source and Accumulating Triglycerides

*Rhodosporidium toruloides* CECT13007 cells grown in solid YPG medium (composition on the basis of 1 liter: yeast extract 10 g; bacteriological peptone 20 g, crude glycerin 47 g; agar, 20 g) were used to inoculate 50 mL of the same medium. After 24 hours of incubation in an orbital shaker (200 rpm, 28° C.), 25 mL of this culture were transferred to 1-liter flasks containing 250 mL of YPG. The cells were incubated again for 24 hours in an orbital shaker (200 rpm, 28° C.). Then, 150 mL of this culture were transferred to a fermenter containing 1.35 liters of MEM medium. This medium consists of (on the basis of 1 liter): crude glycerin, 47 g; yeast extract, 1.5 g; monopotassium phosphate, 0.75 g; ammonium nitrate, 0.28 g; $CaCl_2.2H_2O$, 0.4 g; and $MgSO_4.72H_2O$, 0.4 g, adjusted to pH 5 with concentrated HCl.

The fermenter was maintained at 28° C., the concentration of dissolved oxygen was maintained over 20% by maintaining a stirring at 250 rpm. After 72 hours the concentration of biomass in the fermenter was 24.4 g/L and the intracellular triglyceride content was 52.3%. The composition of fatty acids present was analyzed by means of gas chromatography, a majority amount of palmitic acid (24%), stearic acid (8%), oleic acid (55%) and linoleic acid (2%) being observed.

The cells were harvested by centrifugation and dried at 50° C. for 8 hours.

10 g of biomass (5.2 g of triglycerides) and 100 mL of acid solution in methanol were added in a round-bottomed flask equipped with a condenser. The suspension was heated at 60° C. with vigorous stirring at atmospheric pressure for 20 hours. Once the reaction had ended, the stirring was stopped and the mixture was separated by means of centrifugation. Two phases were obtained: a light phase, containing the methyl esters and methanol in excess, and a heavy phase formed by glycerin, remains of methanol, catalyst and salts.

The purification of the light phase was performed by means of two washings with alkaline water containing sodium hydroxide at a concentration of 0.1% by weight over the water added. In each washing, it was allowed to decant until achieving a good separation of the organic and aqueous phase. The aqueous phase was removed and the methyl esters were collected to eliminate the methanol and water remains by means of evaporation in a vacuum falling film evaporator at an absolute pressure of 100 mbar and 120° C. of temperature. The final amount obtained was 5.09 g of methyl esters, which represents a yield of 98%.

The methyl esters thus obtained are suitable for their use as an automotive fuel in diesel engines complying with the specifications of the European Standard 14214 for this type of fuel (see Table 1).

TABLE 1

| Properties as fuel of the mixture of methyl esters of SCO | | |
|---|---|---|
| Parameter | Units | Result |
| Density at 15° C. | Kg/m³ | 924 |
| Density at 40° C. | Kg/m³ | 4.92 |
| Flash point | ° C. | 173 |
| Sulfur Content | mg/Kg | 6.6 |
| Carbon residue (10% distillation residue) | % (m/m) | 0.33 |

TABLE 1-continued

| Properties as fuel of the mixture of methyl esters of SCO | | |
|---|---|---|
| Parameter | Units | Result |
| Cetane number | | 63.5 |
| water | mg/Kg | 378 |
| Sulphated ash | % (m/m) | 0.01 |
| Total contamination | mg/Kg | 8 |
| Copper corrosion | Class 1 | 1B |
| Oxidation stability | hours | 0.2 |

4. Obtaining Biodiesel from a Mixture of Oleaginous Seeds and Biomass

*Rhodosporidium toruloides* CECT13006 biomass obtained according to the process described in the previous example, and with an intracellular triglyceride content of 53.4%, was mixed with sunflower seeds in the following (seeds/biomass) ratios: 90/10, 80/20 and 75/25. The fat was extracted by extrusion using a press (oil expeller XP100, Alban Blanch). To perform the transesterification, the catalyst (sodium methoxide) was prepared by means of mixing 0.27 liters of methanol and 3 grams of sodium hydroxide. The oil was weighed in a reactor and heated until reaching 50° C. with constant stirring. The catalyst was then added and the reaction was allowed to proceed for 60 minutes. After this time, the stirring was stopped and the phases were separated by centrifugation. The methyl esters were purified according to the steps indicated in the previous example. The yield reached in the tests conducted with the different ratios of seeds and biomass was greater than 98%.

The analysis of the biodiesel obtained showed results that were virtually similar to those obtained in the event of using only the sunflower seeds and the parameters comply with the requirements established by the standard EN14214.

5. Obtaining Biodiesel from the Oil Extracted from the Oleaginous Biomass

Ten grams of *Rhodosporidium toruloides* CECT 13006 strain cells, containing 53.7% fat, were resuspended in 20 mL of demineralized water. Then, 2.5 mL of a 25% ammonium hydroxide solution were added, it was gently stirred and incubated in a bath at 60° C. for 15 minutes. The mixture was cooled and 10 mL of ethanol were added, stirring vigorously. 40 mL of ethyl ether were added and it was stirred again, then 40 mL of petroleum ether were added, being stirred again. The mixture was centrifuged at 6,000 rpm and the light (organic) phase was separated to a previously weighed flat-bottomed spherical flask. The extraction was repeated using half of volume in each case and the extracted fat was mixed in the same flat-bottomed spherical flask. To eliminate possible ethanol or water remains, the flask was subjected to a nitrogen stream for 1 hour. The amount of triglyceride obtained was 5.12 grams.

The transesterification was performed according to the process described in the previous example, a yield of 98.7% being reached. The analysis of the biodiesel obtained complies with all the parameters required by the standard EN14214.

The invention claimed is:

1. An isolated and biologically pure strain of *Rhodosporidium toruloides* CECT 13006 or *Rhodosporidium toruloides* CECT 13007 capable of accumulating triglycerides using glycerin as carbon source.

2. The microorganism according to claim 1, wherein said strain is *Rhodosporidium toruloides* CECT 13007.

3. A process for obtaining biodiesel comprising:
   a) culturing *Rhodosporidiurn toruloides* CECT 13006 or *Rhodosporidiurn toruloides* CECT 13007 to obtain a microbial biomass with a triglyceride content equal to or greater than 20% by dry weight; and
   b) transesterifying the triglycerides of the biomass obtained in step a) with an alcohol into a mixture of fatty acid esters suitable for biodiesel.

4. The process according to claim 3, comprising the additional step of separating the triglycerides in the biomass obtained in section a) from the rest of the biomass then transesterifying these separated triglycerides into a mixture of fatty acid esters according to step b).

5. The process according to claim 4, additionally comprising adding oleaginous plant seeds to the biomass obtained in step a) as a step prior to the transesterification into a mixture of fatty acid esters according to step b).

6. The process according to claim 3, additionally comprising adding oleaginous plant seeds to the biomass obtained in step a) as a step prior to the transesterification into a mixture of fatty acid esters according to step b).

7. A process for obtaining biodiesel, said process comprising:
   a) culturing *Rhodosporidiurn toruloides* CECT 13006 or *Rhodosporidiurn toruloides* CECT 13007 to obtain a microbial biomass with a triglyceride content equal to or greater than 20% by dry weight;
   b) optionally, separating the triglycerides from the microbial biomass;
   c) transesterifying the triglycerides contained in the biomass obtained in step a) or the triglycerides separated in step b) into a mixture of fatty acid esters by means of alcoholysis with an alcohol in acid medium, to produce a first organic phase comprising fatty acid esters and a first aqueous phase;
   d) separating the first organic phase comprising fatty acid esters from the first aqueous phase obtained in step c);
   e) neutralizing the pH of first organic phase comprising the fatty acid esters separated in step d), to obtain a second organic phase comprising neutralized fatty acid esters and a second aqueous phase;
   f) separating the second organic phase comprising neutralized fatty acid esters from the second aqueous phase obtained in step e); and
   g) purifying the second organic phase comprising neutralized fatty acid esters separated in step f) to obtain a mixture of fatty acid esters suitable for biodiesel.

\* \* \* \* \*